(12) United States Patent
Son et al.

(10) Patent No.: US 11,306,043 B2
(45) Date of Patent: Apr. 19, 2022

(54) METHOD FOR PREPARING PARAFFIN

(71) Applicants: SK Innovation Co., Ltd., Seoul (KR); SK Global Chemical Co., Ltd., Seoul (KR)

(72) Inventors: Sungreal Son, Daejeon (KR); Jisun Choi, Daejeon (KR); Chansaem Park, Daejeon (KR); Hyo Seung Park, Daejeon (KR); In Hyoup Song, Daejeon (KR); Woo Sung Jung, Daejeon (KR); Jae Suk Choi, Daejeon (KR); Daehyun Choo, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 16/959,305

(22) PCT Filed: Nov. 9, 2018

(86) PCT No.: PCT/KR2018/013598
§ 371 (c)(1),
(2) Date: Jun. 30, 2020

(87) PCT Pub. No.: WO2019/135484
PCT Pub. Date: Jul. 11, 2019

(65) Prior Publication Data
US 2020/0369579 A1    Nov. 26, 2020

(30) Foreign Application Priority Data

Jan. 2, 2018 (KR) .................. 10-2018-0000292

(51) Int. Cl.
*C07C 5/03* (2006.01)
*C07C 7/04* (2006.01)
(Continued)

(52) U.S. Cl.
CPC .............. *C07C 5/03* (2013.01); *C07C 7/04* (2013.01); *C07C 7/12* (2013.01); *C07C 7/14* (2013.01); *C07C 9/22* (2013.01); *C07C 2523/755* (2013.01)

(58) Field of Classification Search
CPC .... C07C 5/02; C07C 5/03; C07C 7/04; C07C 7/12; C07C 7/14; C07C 9/22;
(Continued)

(56) References Cited

U.S. PATENT DOCUMENTS

| 5,833,839 A | 11/1998 | Wittenbrink et al. |
| 6,765,106 B2 | 7/2004 | Fenouil et al. |

(Continued)

FOREIGN PATENT DOCUMENTS

| EP | 3360947 A1 * | 8/2018 | ............ C10G 45/02 |
| JP | 2007119487 A | 5/2007 | |

(Continued)

*Primary Examiner* — Youngsul Jeong
*Assistant Examiner* — Jason Y Chong
(74) *Attorney, Agent, or Firm* — The Webb Law Firm

(57) ABSTRACT

The present invention relates to a method for preparing paraffin, and can provide a method for preparing paraffin including a hydrogenation step of by-products of a process for preparing linear alpha olefins. Since the method for preparing paraffin of the present invention can convert the by-products of the process for preparing linear alpha olefins to paraffin at a high conversion ratio, it is possible to increase the added value of the by-products.

12 Claims, 1 Drawing Sheet

(51) Int. Cl.
*C07C 7/12* (2006.01)
*C07C 7/14* (2006.01)
*C07C 9/22* (2006.01)

(58) Field of Classification Search
CPC .. C07C 2523/755; B01J 23/755; C10G 50/00; C10G 50/02; C10G 69/126; C10G 70/02
See application file for complete search history.

(56) References Cited

U.S. PATENT DOCUMENTS

| | | | |
|---|---|---|---|
| 7,553,999 B2 | 6/2009 | Elomari et al. | |
| 7,556,728 B2 * | 7/2009 | Lehtonen | C07C 5/03 208/144 |
| 7,572,944 B2 | 8/2009 | Elomari et al. | |
| 8,309,779 B2 * | 11/2012 | Han | B01J 31/2409 585/513 |
| 9,765,010 B2 | 9/2017 | Hategan et al. | |
| 10,322,980 B2 | 6/2019 | Jeon et al. | |
| 10,550,047 B2 | 2/2020 | Wagner et al. | |
| 2010/0081777 A1 * | 4/2010 | Gao | B01J 31/189 526/145 |
| 2010/0298616 A1 * | 11/2010 | Kettunen | C10G 45/64 585/277 |

FOREIGN PATENT DOCUMENTS

| | | |
|---|---|---|
| JP | 2007269885 A | 10/2007 |
| KR | 19990071950 A | 9/1999 |
| KR | 1020080079316 A | 8/2008 |
| KR | 1020090089355 A | 8/2009 |
| KR | 1020150123547 A | 11/2015 |
| KR | 1020160005866 A | 1/2016 |
| KR | 1020160065709 A | 6/2016 |
| KR | 1020170066399 A | 6/2017 |
| WO | 2016122949 A1 | 8/2016 |

* cited by examiner

[FIG. 1]
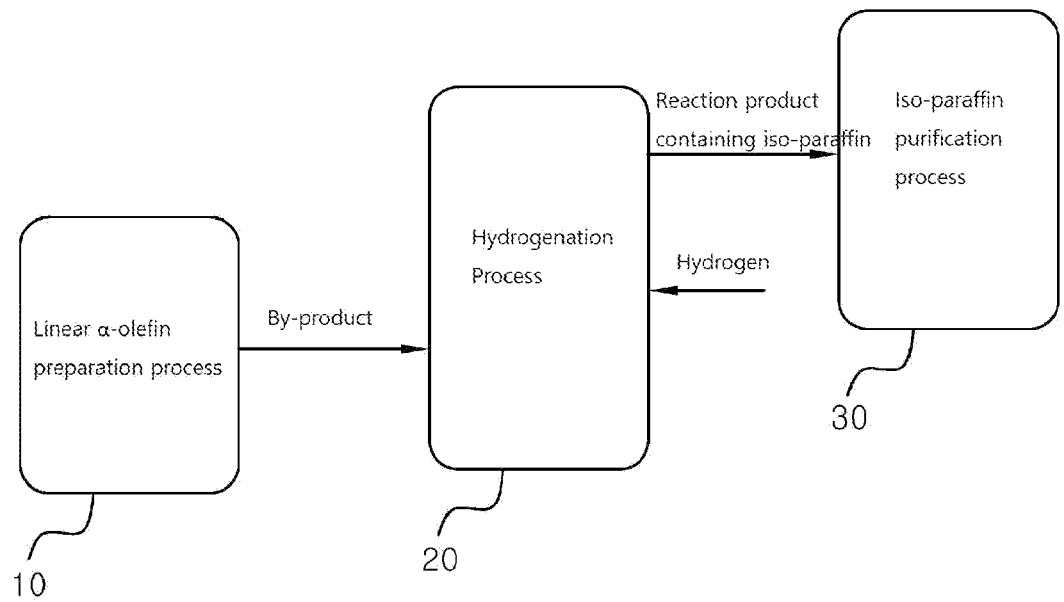
[FIG. 2]
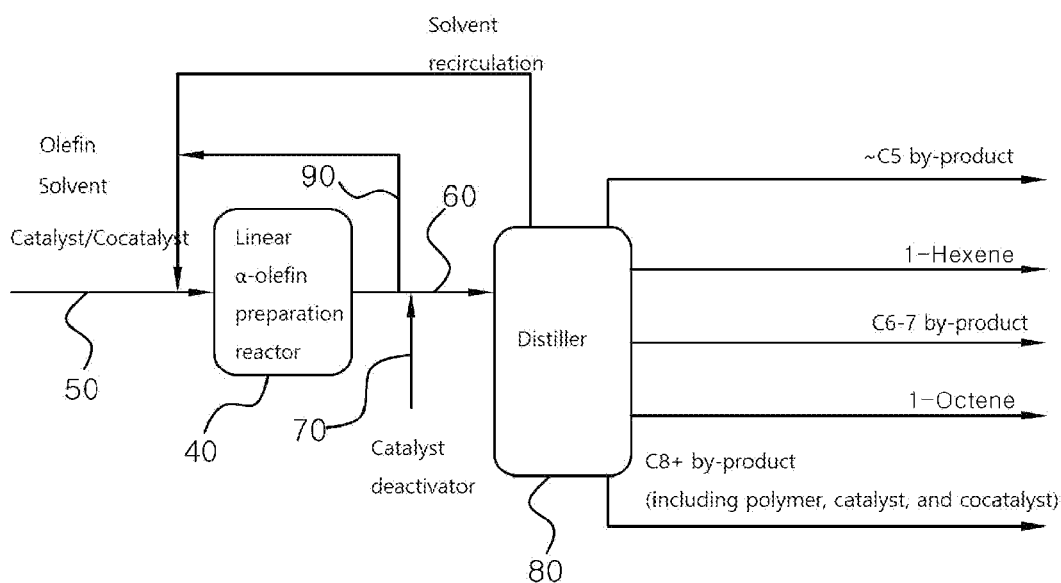

METHOD FOR PREPARING PARAFFIN

CROSS-REFERENCE TO RELATED APPLICATIONS

This application is the United States national phase of International Application No. PCT/KR2018/013598 filed Nov. 9, 2018, and claims priority to Korean Patent Application No. 10-2018-0000292 filed Jan. 2, 2018, the disclosures of which are hereby incorporated by reference in their entirety.

TECHNICAL FIELD

The present invention relates to a preparation method of paraffin, and more particularly, to a preparation method of paraffin from by-products of a linear α-olefin preparation process.

BACKGROUND ART

Ethylene is a raw material used as a basic raw material in the chemical industry so that the production amount and the consumption amount thereof are regarded as an indicator of a national chemical industry scale. Usually, ethylene is used as a monomer for preparing polymers such as polyethylene, and in some cases, is used for preparation of various chemical materials by adjusting a polymerization degree to prepare a linear α-olefin (LAO) having a carbon length (chain) of about C4 to C40.

In the linear α-olefin preparation process as such, branched olefins, linear internal olefins, iso-paraffin, n-paraffin, and naphthene are produced as by-products. These may be utilized as a fuel, but the value thereof is very low.

Thus, a plan for adding a high value to the by-products of the linear α-olefin preparation process, is needed.

DISCLOSURE

Technical Problem

An object of the present invention is to provide a preparation method of paraffin by converting by-products of a linear α-olefin preparation process into paraffin at a high conversion rate to add a high value to the by-product to improve economic feasibility.

Technical Solution

In one general aspect, a preparation method of paraffin includes providing a feed including 30 to 100 mol % of a branched olefin, 0 to 50 mol % of a linear internal olefin, and a balance of other by-products; and hydrogenating the feed.

In the preparation method of paraffin according to an embodiment of the present invention, the feed may be directly hydrogenated.

The feed may include 60 to 95 mol % of the branched olefin and 1 to 20 mol % of the linear internal olefin.

Other by-products may include iso-paraffin, n-paraffin, naphthene, or a combination thereof.

The branched olefin may be a C4 to C20 branched olefin.

The hydrogenation may be performed in a trickle bed reactor.

The feed flows into the reactor in a liquid phase, and a space velocity (SV) at which the feed flows may be 0.1 to 4 $h^{-1}$.

The hydrogenation may be performed at a temperature of 100 to 200° C. under a pressure of 10 to 100 $kg/cm^2g$ under a metal catalyst selected from the group consisting of nickel (Ni), platinum (Pt), palladium (Pd), rhodium (Rh), ruthenium (Lu), and an alloy two or more thereof.

After the hydrogenation, separating the thus-prepared paraffin may be further included.

After the hydrogenation, separating iso-paraffin from the thus-prepared paraffin may be further included.

Advantageous Effects

According to the preparation method of paraffin of an embodiment of the present invention, the by-products of the linear α-olefin preparation process may be converted into paraffin at a high conversion rate, it is possible to add a high value to the by-product.

In addition, since a large amount of a branched olefin is included in the by-products of the linear α-olefin preparation process, it is possible to produce an iso-paraffin solvent which is a commercially available chemical product used in various fields and the effect of adding a high value to the by-product may be maximized, by converting the by-products into paraffin.

DESCRIPTION OF DRAWINGS

FIG. 1 is an exemplary flowchart of a preparation method of iso-paraffin of an embodiment of the present invention.

FIG. 2 is a schematic diagram which more specifically illustrates a linear α-olefin preparation process 10 in an embodiment of the present invention.

BEST MODE

Unless otherwise defined herein, all terms used in the specification (including technical and scientific terms) may have the meaning that is commonly understood by those skilled in the art. Throughout the present specification, unless explicitly described to the contrary, a part "comprising" any elements will be understood to imply further inclusion of other elements rather than the exclusion of any other elements. In addition, unless explicitly described to the contrary, a singular form includes a plural form herein.

Throughout the present specification, "paraffin" refers to a C4 to C50 saturated hydrocarbon, unless otherwise explicitly defined.

An embodiment of the present invention provides a preparation method of paraffin from by-products of a linear α-olefin preparation process, the method including a step of hydrogenating the by-products of the linear α-olefin preparation process.

As described above, branched olefins, linear internal olefins, iso-paraffin, n-paraffin, and naphthene are produced as by-products in the linear α-olefin preparation process, and these may be utilized as a fuel, but the value thereof is very low, and thus, it is necessary to add a high value to the by-products.

According to the preparation method of paraffin of an embodiment of the present invention, it is possible add a high value to the by-products by preparing paraffin by a hydrogenation process, using the by-products of the linear α-olefin preparation process as a feed.

Specifically, the by-products of the linear α-olefin preparation process may include 30 to 100 mol % of the branched olefin, 0 to 50 mol % of the linear internal olefin, and 0 to 30 mol % of other by-products including iso-paraffin, n-paraffin, naphthene, and the like, based on a total of 100 mol % of the by-products.

More specifically, the by-products may include 40 to 95 mol %, 50 to 95 mol %, or 60 to 95 mol % of the branched olefin, 1 to 40 mol %, 1 to 30 mol %, or 1 to 20 mol % of the linear internal olefin, and a balance of other by-products including iso-paraffin, n-paraffin, naphthene, and the like.

Since the by-products of the linear α-olefin preparation process is hydrogenated to produce paraffin, and the thus-prepared branched iso-paraffin and linear paraffin products may be used as a raw material in various industry fields, it is possible to add a high value to the by-products.

Since the thus-prepared paraffin is a material which may be used in a wide variety of fields, high-value addition is possible, as compared with the case of using the by-products of the linear α-olefin preparation process as a fuel.

Furthermore, the branched olefin by-products may include C4 to C20, and more specifically C6 to C20 branched olefin, and an iso-paraffin solvent prepared by hydrogenation of the branched olefin may be subjected to higher-value addition as a commercially available chemical product which is utilized in various fields such as additives, paints, coating agents, reaction solvents, and agrochemical fields.

In the step of hydrogenating of the preparation method of paraffin of an embodiment of the present invention, the by-products of the linear α-olefin preparation process may be directly hydrogenated.

Here, "being directly hydrogenated" means that the by-products occurring in the linear α-olefin preparation process themselves are subjected to a step of hydrogenating without a further treatment process of causing a chemical reaction such as isomerization.

As described above, since the by-products of the linear α-olefin preparation process include 30 mol % or more, more specifically 40 mol % or more, 50 mol % or more, or 60 mol % or more of the branched olefin which is a large amount and 50 mol % or less, more specifically 40 mol % or less, 30 mol % or less, or 20 mol % or less of the linear internal olefin, the by-products may be directly hydrogenated without a separate isomerization process to allow higher-value addition and manufacture of an iso-paraffin product which may be industrially directly used.

Of course, in an embodiment of the present invention, the case of separating and removing the linear internal olefin by a simple separation process which does not cause a chemical reaction, before a hydrogenation process, is not excluded.

In the preparation method of paraffin of an embodiment of the present invention, the step of hydrogenating may be performed at a temperature of 100 to 200° C. under a pressure of 10 to 100 kg/cm$^2$g under a hydrogenation catalyst. However, the present invention is not limited thereto.

In addition, the step of hydrogenating is not limited to a certain reactor type, and may be performed using various reactors such as a batch reactor, a continuous stirred tank reactor (CSTR), a continuous plug flow reactor (PFR), a fixed bed reactor, and a trickle bed reactor.

In an embodiment of the specific step of hydrogenating, for example, the hydrogenation may be performed by continuously injecting by-products of the linear α-olefin preparation process in a liquid phase to a reactor filled with a catalyst, in which the pressure described above is maintained by hydrogen supplied into the reactor, but not limited thereto.

In a more specific embodiment, the hydrogenation may be performed by continuously injecting liquid by-products of the linear α-olefin preparation process to a trickle bed reactor filled with a catalyst and hydrogen in a countercurrent direction or a concurrent direction. The trickle bed reactor allows excellent contact of the catalyst filled therein and the liquid by-products, and has excellent reaction efficiency.

In addition, if necessary, the reactor may be provided as two or more reactors, but which is only an example and it is not intended to limit the present invention.

Here, a space velocity (SV) at which the liquid by-products flow in may be 0.1 to 4 h$^{-1}$, more specifically 0.5 to 3 h$^{-1}$, or 1 to 2 h$^{-1}$. The space velocity of the by-products herein may be calculated by dividing an inflow rate (m$^3$/h) of the by-products by a reaction volume (m$^3$) in the reactor, and the reaction volume means a space in the reactor excluding a room filled with a catalyst, in which the by-products may flow. Within the range, the hydrogenation reaction efficiency is excellent, and the yield of iso-paraffin may be increased.

As the hydrogenation catalyst, more specifically, a catalyst in the form in which a metal catalyst is supported on a support assisting catalytic activity, may be used.

Here, the metal catalyst may be nickel (Ni), platinum (Pt), palladium (Pd), rhodium (Rh), ruthenium (Lu), or an alloy containing two or more thereof such as a platinum-palladium alloy, and the support may be alumina ($Al_2O_3$), silica ($SiO_2$), titania ($TiO_2$), zirconia ($ZrO_2$), zeolite, clay materials, or a combination thereof, but is not limited thereto.

In addition, the support amount of the metal catalyst supported on the support may be, as an example, 10 to 40 wt %, and more specifically 15 to 30 wt %, based on 100 wt % of the catalyst in which the metal catalyst is supported on the support.

The preparation method of paraffin of an embodiment of the present invention may further include a step of separating the thus-prepared paraffin after the step of hydrogenating.

This step may be a step of hydrogenating by-products of the linear α-olefin preparation process to prepare paraffin, and then separating the prepared paraffin from remaining reactants of the linear α-olefin preparation process, a reaction additive such as a catalyst, a catalyst deactivator for terminating the reaction, remaining reactants of the step of hydrogenating, a reaction additive such as a catalyst, and the like which are included in the thus-obtained product.

A specific method of performing this step is not limited to a certain manner as long as the prepared paraffin may be separated, and may be appropriately selected from distillation, adsorption, crystallization, extraction, or a combination thereof, depending on the process embodiment.

In addition, the preparation method of paraffin of an embodiment of the present invention may further include a step of separating iso-paraffin from the thus-prepared paraffin after the step of hydrogenating.

This step may be a step of separating iso-paraffin to which higher value may be added from a paraffin product in which a linear paraffin and the like are mixed with iso-paraffin.

A specific method of performing this step is not limited to a certain manner as long as the prepared iso-paraffin may be separated, and may be appropriately selected from distillation, adsorption, crystallization, extraction, or a combination thereof, depending on the process embodiment.

In addition, the order of a step of separating paraffin prepared after the step of hydrogenating as described above; and a step of separating iso-paraffin from the paraffin prepared after the step of hydrogenating is not limited to a certain order, and the prepared paraffin is separated first, and then specifically the iso-paraffin is separated, or the iso-paraffin is separated first, and then a further purification process is performed for further purifying the separated iso-paraffin.

FIG. 1 is an exemplary flowchart of a preparation method of iso-paraffin of an embodiment of the present invention. Hereinafter, additional description of the present invention will be provided with reference to FIG. 1. However, the present invention is not limited to a process embodiment of FIG. 1.

The liquid by-product having the contents described above as the by-products of the linear α-olefin preparation process is introduced to a hydrogenation process (20). The by-products in the hydrogenation process 20 may be hydrogenated to produce iso-paraffin. Thereafter, the thus-prepared iso-paraffin-containing reaction product is introduced to an iso-paraffin purification process 30, is subjected to a process of separating paraffin and/or iso-paraffin in the reaction product, and is finally commercialized. Specific embodiments of the hydrogenation process 20 and the iso-paraffin purification process 30 are as described above.

In an embodiment of the present invention, FIG. 2 is a schematic diagram illustrating the linear α-olefin preparation process 10 more specifically, and an exemplary embodiment of the linear α-olefin preparation process 10 will be described referring to FIG. 2.

First, a plant of a linear α-olefin preparation process 10 may include a linear α-olefin preparation reactor 40 for performing oligomerization, an injection line 50 for injecting an olefin and a catalyst composition to the linear α-olefin preparation reactor 40, an outflow line 60 for outflow of an oligomerization reaction product from the linear α-olefin preparation reactor 40, a catalyst deactivator injection line 70 for introducing a catalyst deactivator to the outflow line 60, a distiller 80 for separating the oligomerization reaction product, and a recirculation line 90 for recirculating an unreacted olefin in effluent discharged to the outflow line 60, in which the catalyst composition is an olefin oligomerization catalyst composition described later and may include a transition metal source and a heteroatom ligand or an oligomerization transition metal catalyst prepared therefrom, a cocatalyst, and a solvent.

The linear α-olefin preparation reactor 40 may include a batch reactor, a semi-batch reactor, and a continuous reactor, but is not limited thereto.

The distiller 80 is not limited to a certain type of distiller, and the number of columns of a distillation tower may be adjusted as required. A distillation manner is also not limited to a certain distillation manner, and an appropriate distillation method may be adopted as required. As an example, a plurality of distillation towers which includes a bottom reboiler (BTM reboiler) and an overhead condenser (OVHD condenser) and 50 or more and 100 or less columns, may be used.

In addition, though not shown in FIG. 2, when an oxygen-containing inorganic material, which is described later as the catalyst deactivator and is in a gaseous state at 25° C. and 1 atm, is used, an adsorption tower (not shown) may be further provided on the recirculation line 90. Thus, most of the unreacted catalyst deactivator may be removed by adsorption during recirculation of unreacted olefin.

As the adsorption tower (not shown), an adsorption tower filled with an adsorbent which is included in the catalyst deactivator and may adsorb the oxygen-containing inorganic material in a gaseous state at 25° C. and 1 atm, may be used.

The number of adsorption towers may be adjusted as required, and is not particularly limited. As a non-limiting example of the adsorbent, a metal oxide or a zeolite adsorbent as an adsorbent which can adsorb and remove the oxygen-containing inorganic material may be adopted, and as a specific example, a copper oxide such as CuO and $Cu_2O$, or Zeolite 4A may be adopted.

In the embodiment of specific paraffin preparation of the present invention, the by-product introduced to a hydrogenation process 20 in the linear α-olefin preparation process 10 may be directly obtained from the linear α-olefin preparation reactor 40 in the linear α-olefin preparation process 10 or may be a by-product remaining after recovery of some products such as 1-hexene and 1-octene by distillation from the distiller 80. More preferably, the by-product may be a by-product remaining after recovery of some products such as 1-hexene and 1-octene by distillation, and when iso-paraffin is prepared according to an embodiment of the present invention from by-products containing a large amount of branched α-olefin remaining after first separating a product capable of high-value addition, high-value addition of the entire process may be further maximized, which is thus preferred.

Hereinafter, the linear α-olefin preparation process which is a source of the by-product used in the preparation of paraffin of an embodiment of the present invention will be described in more detail. However, this is an example and the present invention is not necessarily limited thereto.

The linear α-olefin preparation process may include a step of oligomerizing an olefin monomer in the presence of a transition metal catalyst, a cocatalyst, and a solvent.

The solvent may be an inert solvent. That is, an oligomerization transition metal catalyst, a cocatalyst, and an optional inert solvent which does not react with a catalyst deactivator may be used, and the inert solvent may include an aliphatic hydrocarbon. The aliphatic hydrocarbon is a saturated aliphatic hydrocarbon, and may include a linear saturated aliphatic hydrocarbon represented by $C_nH_{2n+2}$ (wherein n is an integer of 1 to 15), an alicyclic saturated aliphatic hydrocarbon represented by $C_mH_{2m}$ (wherein m is an integer of 3 to 8), and a saturated aliphatic hydrocarbon in which one or two or more lower alkyl groups having 1 to 3 carbon atoms are substituted. Specific list thereof is one or more selected from the group consisting of hexane, heptane, octane, nonene, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethyhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but is not limited thereto.

A reaction temperature of the oligomerization reaction step may be a temperature of 0 to 200° C., specifically a temperature of 15 to 130° C., more specifically a temperature of 40 to 100° C., but is not limited thereto. A reaction pressure may be an atmospheric pressure to 500 bar, specifically an atmospheric pressure to 100 bar, and more specifically an atmospheric pressure to 80 bar. However, the present invention is not limited thereto.

The transition metal catalyst may be directly prepared and used, or an oligomerization catalyst which is commercially available may be used as the transition metal catalyst, or constituent components for preparing the transition metal catalyst, that is, a transition metal source and a heteroatom ligand may be used.

The transition metal source according to an embodiment of the present invention may be a transition metal inorganic salt, a transition metal organic salt, a transition metal coordination compound, or a composite of a transition metal and an organic metal, and the transition metal of the transition metal source may be Group 4, 5, or 6 transition metals, specifically chromium, molybdenum, tungsten, titanium, tantalum, vanadium, or zirconium, and preferably chromium.

As an example, the transition metal source may bind to a transition metal and various organic ligands and the organic ligand as such may be selected from the following structures:

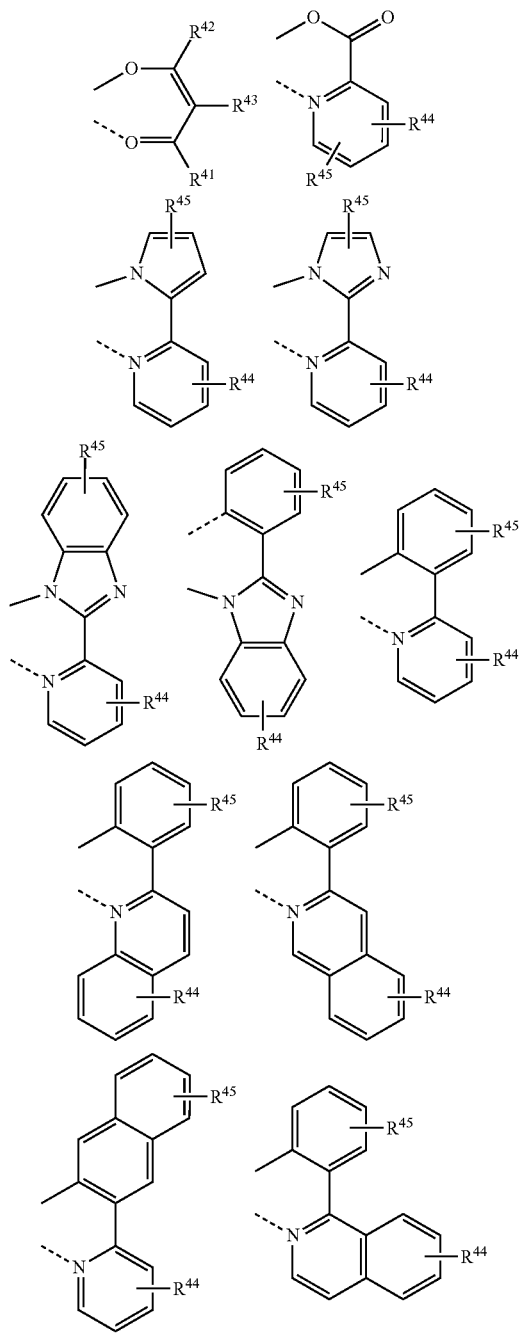

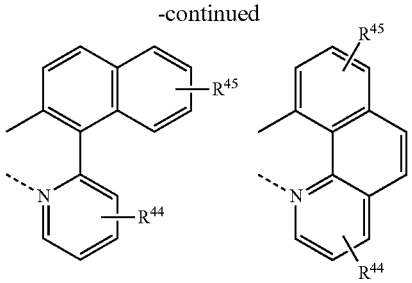

wherein $R^{41}$ to $R^{45}$ are independently of one another hydrocarbyl, substituted hydrocarbyl, heterohydrocarbyl, or substituted heterohydrocarbyl.

Preferably, the organic ligand may be an acetylacetonate-based ligand represented by the following Chemical Formula 2:

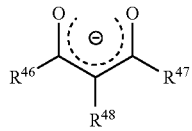

[Chemical Formula 2]

wherein $R^{46}$ to $R^{48}$ are independently of one another hydrogen, a halogen, (C6-C20)aryl, (C6-C20)ar(C1-C10)alkyl, (C1-C10)alkyl, halo(C1-C10)alkyl, (C6-C20)ar(C2-C10)alkenyl, (C2-C10)alkenyl, (C6-C20)ar(C2-C10)alkynyl, (C2-C10)alkynyl, (C1-C10)alkoxy, (C6-C20)aryloxy, (C1-C10)alkylcarbonyloxy, (C2-C10)alkenylcarbonyloxy, (C2-C10)alkynylcarbonyloxy, (C3-C7)cycloalkyl, (C1-C10)alkylsilyl, (C2-C10)alkenylsilyl, fluorine-substituted (C2-C10)alkynylsilyl, (C6-C20)arylsilyl, (C3-C20)heteroaryl, or 5- to 7-membered heterocycloalkyl; and the aryl, aralkyl, alkyl, aralkenyl, alkenyl, aralkynyl, alkynyl, alkoxy, aryloxy, cycloalkyl, heteroaryl, and heterocycloalkyl of $R^{46}$ to $R^{48}$ may be further substituted by one or more selected from the group consisting of (C1-C10)alkyl, (C2-C10)alkenyl, (C2-C10)alkynyl, (C1-C10)alkoxy, (C6-C20)aryl, (C6-C20)aryloxy, and halogens.

Preferably, in Chemical formula 2, $R^{46}$ and $R^{47}$ may be independently of each other hydrogen, a halogen, or halo (C1-C10)alkyl, and $R^{48}$ may be hydrogen or (C1-C10)alkyl.

The acetylacetonate-based ligand of Chemical Formula 2 according to an exemplary embodiment of the present invention may be selected from the following structures, but is not limited thereto:

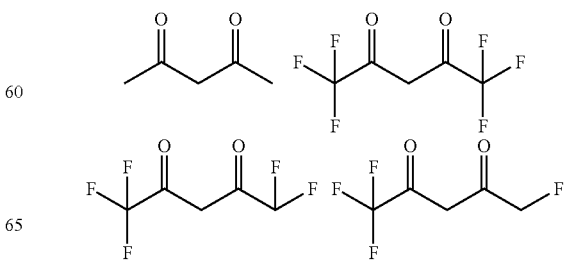

-continued

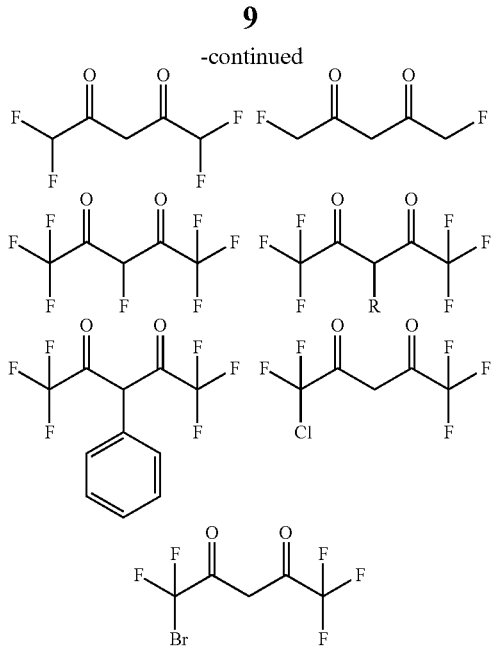

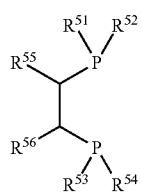

As a specific example of the transition metal source, when the transition metal is chromium, it may be one or two or more selected from the group consisting of chromium(III) acetylacetonate, chromium(III) chloride, chromium(III) naphthenate, chromium(III) 2-ethylhexanoate, chromium (III) acetate, chromium(III) 2,2,6,6-tetramethylheptadionate, chromium(III) octanoate, and chromium hexacarbonyl, and preferably, may be chromium(III) acetylacetonate or chromium(III) chloride.

Preferably, the heteroatom ligand according to an exemplary embodiment of the present invention may be $(R)_nB—C-D(R)_m$ wherein B and D are independently of each other any one selected from the group consisting of phosphorus, arsenic, antimony, oxygen, bismuth, sulfur, selenium, and nitrogen; C is a linking group between B and D; R is identical to or different from each other and independently of each other selected from the group consisting of hydrocarbyl, hetero hydrocarbyl, substituted hydrocarbyl, and substituted hetero hydrocarbyl; n and m may be determined by each of valence and oxidation state of B or D; and preferably B and D are independently of each other phosphorus; C is a linking group between B and D and alkylene or N(R') (wherein R' is alkyl), R may be identical to or different from each other and independently of each other selected from the group consisting of hydrocarbyl, hetero hydrocarbyl, substituted hydrocarbyl, and substituted hetero hydrocarbyl; and n and m may be determined by each of valance and oxidation state of B or D.

The heteroatom ligand may have a P—C—C—P skeleton structure represented by the following Chemical formula 3 or a P—N—P skeleton structure represented by the following Chemical Formula 4, but is not limited thereto:

[Chemical Formula 3]

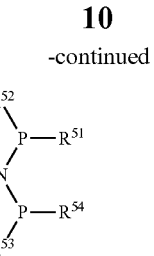

[Chemical Formula 4]

wherein
$R^{51}$ to $R^{54}$ independently of one another hydrocarbyl, substituted hydrocarbyl, heterohydrocarbyl, or substituted heterohydrocarbyl; and
$R^{55}$ and $R^{56}$ are independently of each other hydrocarbyl or substituted hydrocarbyl, or $R^{55}$ and $R^{56}$ may be bonded to each other via hydrocarbylene, substituted hydrocarbylene, heterohydrocarbylene, or substituted heterohydrocarbylene to form a ring.

In Chemical Formulae 3 and 4, $R^{51}$ to $R^{54}$ are independently of one another (C6-C20)aryl, (C6-C20)ar(C1-C10) alkyl, (C6-C20)ar(C2-C10)alkenyl, (C6-C20)ar(C2-C10) alkynyl, (C1-C10)alkyl, (C2-C10)alkenyl, (C2-C10) alkynyl, (C1-C10)alkoxy, (C6-C20)aryloxy, (C1-C10) alkoxycarbonyl, (C1-C10)alkylcarbonyloxy, (C2-C10) alkenylcarbonyloxy, (C2-C10)alkynylcarbonyloxy, aminocarbonyl, (C1-C10)alkylcarbonylamino, (C2-C10) alkenylcarbonylamino, (C2-C10)alkynylcarbonylamino, (C3-C7)cycloalkyl, thio(C1-C10)alkyl, thio(C2-C10)alkenyl, thio(C2-C10)alkynyl, (C1-C10)alkylsilyl, (C2-C10) alkenylsilyl, (C2-C10)alkynylsilyl, (C6-C20)arylsilyl, (C3-C20)heteroaryl, 5- to 7-membered heterocycloalkyl, or —$NR^{61}R^{62}$, and $R^{61}$ and $R^{62}$ are independently of each other (C1-C10)alkyl, (C2-C10)alkenyl, (C2-C10)alkynyl, (C6-C20)aryl, di(C1-C10)alkylamino, di(C2-C10)alkenylamino, or di(C2-C10)alkynylamino;

$R^{55}$ and $R^{56}$ are independently of each other (C6-C20) aryl, (C6-C20)ar(C1-C10)alkyl, (C6-C20)ar(C2-C10)alkenyl, (C6-C20)ar(C2-C10)alkynyl, (C1-C10)alkyl, (C2-C10)alkenyl, (C2-C10)alkynyl, (C3-C7)cycloalkyl, (C3-C20)heteroaryl, 5- to 7-membered heterocycloalkyl, (C1-C10)alkoxy, (C6-C20)aryloxy, (C1-C10)alkoxycarbonyl, (C1-C10)alkylcarbonyloxy, (C2-C10)alkenylcarbonyloxy, (C2-C10)alkynylcarbonyloxy, aminocarbonyl, (C1-C10)alkylcarbonylamino, (C2-C10)alkenylcarbonylamino, (C2-C10)alkynylcarbonylamino, di(C1-C10)alkylamino, di(C2-C10)alkenylamino, di(C2-C10)alkynylamino, (C1-C10) alkylsilyl, (C2-C10)alkenylsilyl, (C2-C10)alkynylsilyl, or (C6-C20)arylsilyl, or $R^{55}$ and $R^{56}$ may be bonded via (C3-C10)alkylene or (C3-C10)alkenylene to form a ring;

the aryl, aralkyl, aralkenyl, aralkynyl, alkyl, alkenyl, alkoxy, aryloxy, alkoxycarbonyl, alkylcarbonyloxy, alkenylcarbonyloxy, alkynylcarbonyloxy, cycloalkyl, heteroaryl, and heterocycloalkyl of $R^{51}$ to $R^{54}$, and the aryl, aralkyl, aralkenyl, aralkynyl, alkyl, alkenyl, cycloalkyl, heteroaryl, heterocycloalkyl, alkoxy, aryloxy, alkoxycarbonyl, alkylcarbonyloxy, alkenylcarbonyloxy, alkynylcarbonyloxy, aminocarbonyl, alkylcarbonylamino, alkenylcarbonylamino, alkynylcarbonylamino, dialkylamino, dialkenylamino, dialkynylamino, alkylsilyl, alkenylsilyl, alkynylsilyl, or arylsilyl of $R^{55}$ and $R^{56}$ may be further substituted by one or more selected from the group consisting of (C1-C10)alkyl, (C2-C10)alkenyl, (C2-C10)alkynyl, (C1-C10)alkoxy, (C6-C20)aryloxy, di(C1-C10)alkylamino, di(C2-C10)alkenylamino, di(C2-C10)alkynylamino and halogens.

Preferably, in Chemical Formulae 3 and 4, $R^{51}$ and $R^{54}$ are independently of one another (C6-C20)aryl; and $R^{55}$ and $R^{56}$ may be independently of each other (C1-C10)alkyl.

In Chemical Formulae 3 and 4, specifically, each of $R^{51}$ to $R^{54}$ is phenyl, benzyl, biphenyl, naphthyl, anthracenyl, mesityl, xylyl, methyl, ethyl, ethenyl, ethynyl, n-propyl, i-propyl, propenyl, propynyl, n-butyl, t-butyl, butenyl, butynyl, methylphenyl, ethylphenyl, methoxyphenyl, ethoxyphenyl, isopropylphenyl, isopropoxyphenyl, t-butylphenyl, cumyl, methoxy, ethoxy, phenoxy, tolyloxy, dimethylaminophenyl, cyclopropyl, cyclobutyl, cyclopentyl, cyclohexyl, methylcyclohexyl, ethylcyclohexyl or isopropylcyclohexyl, dimethylamino, thiomethyl, trimethylsilyl, and dimethylhydrazyl;

$R^{55}$ and $R^{56}$ are independently of each other methyl, ethyl, ethenyl, ethynyl, n-propyl, i-propyl, propenyl, propynyl, n-butyl, t-butyl, i-butyl, butenyl, butynyl, phenyl, benzyl, tolyl, xylyl, methoxy, ethoxy, phenoxy, methylamino, or dimethylamino, or $R^{55}$ and $R^{56}$ may be bonded via propylene, butylene, pentylene, or butenylene to form a 5- to 7-membered ring.

The ligand having a P—C—C—P skeleton structure of Chemical Formula 3 may be selected from the group consisting of (phenyl)$_2$P—CH(methyl)CH(methyl)-P(phenyl)$_2$, (4-methoxyphenyl)$_2$P—CH(methyl)CH(methyl)-P(4-methoxyphenyl)$_2$, (4-methylphenyl)$_2$P—CH(methyl)CH(methyl)-P(4-methylphenyl)$_2$, (4-ethylphenyl)$_2$P—CH(methyl)CH(methyl)-P(phenyl)$_2$, (2-ethylphenyl)$_2$P—CH(methyl)CH(methyl)-P(2-ethylphenyl)$_2$, (2-isopropylphenyl)$_2$P—CH(methyl)CH(methyl)P-(2-isopropylphenyl)$_2$, (2-methylphenyl)$_2$P—CH(methyl)CH(methyl)P-(2-methylphenyl)$_2$, (2-ethylphenyl)$_2$P—CH(methyl)CH(methyl)-P(phenyl)$_2$, (3-methoxyphenyl)$_2$P—CH(methyl)CH(methyl)-P(3-methoxyphenyl)$_2$, (4-ethoxyphenyl)$_2$P—CH(methyl)CH(methyl)-P(2-ethoxyphenyl)$_2$, (4-dimethylaminominephenyl)$_2$P—CH(methyl)CH(methyl)-P(4-dimethylaminophenyl)$_2$, (4-ethylcyclohexyl)$_2$P—CH(methyl)CH(methyl)-P(4-ethylcyclohexyl)$_2$, (2-methoxyphenyl)$_2$P—CH(methyl)CH(methyl)-P(2-methoxyphenyl)$_2$, (2-ethoxyphenyl)$_2$P—CH(methyl)CH(methyl)-P(2-ethoxyphenyl)$_2$, (2-dimethylaminophenyl)$_2$P—CH(methyl)CH(methyl)-P(2-dimethylaminophenyl)$_2$, (2-ethylcyclohexyl)$_2$P—CH(methyl)CH(methyl)-P(2-ethylcyclohexyl)$_2$, (4-ethylphenyl)$_2$P—CH(ethyl)CH(methyl)-P(4-ethylphenyl)$_2$, (4-methoxyphenyl)$_2$P—CH(ethyl)CH(methyl)-P(phenyl)$_2$, (2-ethylphenyl)$_2$P—CH(ethyl)CH(methyl)-P(2-ethylphenyl)$_2$, (4-ethylphenyl)$_2$P—CH(ethyl)CH(ethyl)-P(4-ethylphenyl)$_2$, (phenyl)$_2$P—CH(ethyl)CH(ethyl)-P(phenyl)$_2$, (2-ethylphenyl)$_2$P—CH(ethyl)CH(ethyl)-P(2-ethylphenyl)$_2$, (phenyl)$_2$P—CH(isopropyl)CH(methyl)-P(phenyl)$_2$, (4-methoxyphenyl)$_2$P—CH(isopropyl)CH(methyl)-P(4-methoxyphenyl)$_2$, (4-ethylphenyl)$_2$P—CH(isopropyl)CH(methyl)-P(4-ethylphenyl)$_2$, (2-ethylphenyl)$_2$P—CH(isopropyl)CH(methyl)-P(2-ethylphenyl)$_2$, (phenyl)$_2$P—CH(n-propyl)CH(methyl)-P(phenyl)$_2$, (4-methoxyphenyl)$_2$P—CH(n-propyl)CH(methyl)-P(4-methoxyphenyl)$_2$, (4-ethylphenyl)$_2$P—CH(n-propyl)CH(methyl)-P(4-ethylphenyl)$_2$, (2-ethylphenyl)$_2$P—CH(n-propyl)CH(methyl)-P(2-ethylphenyl)$_2$, (phenyl)$_2$P—CH(isopropyl)CH(ethyl)-P(phenyl)$_2$, (4-methoxyphenyl)$_2$P—CH(isopropyl)CH(ethyl)-P(4-methoxyphenyl)$_2$, (4-ethylphenyl)$_2$P—CH(isopropyl)CH(ethyl)-P(4-ethylphenyl)$_2$, (2-ethylphenyl)$_2$P—CH(isopropyl)CH(ethyl)-P(2-ethylphenyl)$_2$, 1,2-di-(P(phenyl)$_2$)cyclohexane, 1,2-di-(P(4-methoxyphenyl)$_2$)cyclohexane, 1,2-di-(P(4-ethylphenyl)$_2$)cyclohexane, 1,2-di-(P(2-ethylphenyl)$_2$)cyclohexane, 1,2-di-(P(phenyl)$_2$)cyclopentane, 1,2-di-(P(4-methoxyphenyl)$_2$)cyclopentane, 1,2-di-(P(4-ethylphenyl)$_2$)cyclopentane, 1,2-di-(P(2-ethylphenyl)$_2$)cyclopentane, (4-ethylphenyl)$_2$P—CH(dimethylamino)CH(dimethylamino)-P(4-ethylphenyl)$_2$, and (2-ethylphenyl)$_2$P—CH(dimethylamino)CH(dimethylamino)-P(2-ethylphenyl)$_2$, but is not limited thereto.

The ligand having a P—N—P skeleton structure of Chemical Formula 4 may be selected from the group consisting of (phenyl)$_2$PN(methyl)P(phenyl)$_2$, (phenyl)$_2$PN(pentyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$PN(p-tbutylphenyl)P(phenyl)$_2$, (Phenyl)$_2$PN((CH$_2$)$_3$—N-morpholine)P(phenyl)$_2$, (phenyl))$_2$PN (Si(CH$_3$)$_3$) P(phenyl)$_2$, (((phenyl)$_2$P)$_2$NCH$_2$CH$_2$)N, (ethyl)$_2$PN(methyl)P(ethyl)$_2$, (ethyl)$_2$PN(isopropyl)P(phenyl)$_2$, (ethyl)(phenyl)PN(methyl)P(ethyl) (phenyl), (ethyl)(phenyl)PN(isopropyl)P(phenyl)$_2$, (phenyl)$_2$P(=Se)N(isopropyl)P(phenyl)$_2$, (phenyl)$_2$PCH$_2$CH$_2$P(phenyl)$_2$, (o-ethylphenyl)(phenyl)PN(isopropyl)P(phenyl)$_2$, (o-methylphenyl)$_2$PN(isopropyl)P(o-methylphenyl) (phenyl), (phenyl)$_2$PN(benzyl)P(phenyl)$_2$, (phenyl)$_2$PN(1-cyclohexylethyl)P(phenyl)$_2$, (phenyl)$_2$PN[CH$_2$CH$_2$CH$_2$Si(OMe$_3$)]P(phenyl)$_2$, (phenyl)$_2$PN(cyclohexyl)P(phenyl)$_2$, (phenyl)$_2$PN(2-methylcyclohexyl)P(phenyl)$_2$, (phenyl)$_2$PN(allyl)P(phenyl)$_2$, (2-naphthyl)$_2$PN(methyl)P(2-naphthyl)$_2$, (p-biphenyl)$_2$PN(methyl)P(p-biphenyl)$_2$, (p-methylphenyl)$_2$PN(methyl)P(p-methylphenyl)$_2$, (2-thiophenyl)$_2$PN(methyl)P(2-thiophenyl)$_2$, (phenyl)$_2$PN(methyl)N(methyl)P(phenyl)$_2$, (m-methylphenyl)$_2$PN(methyl)P(m-methylphenyl)$_2$, (phenyl)$_2$PN(isopropyl)P(phenyl)$_2$, and (phenyl)$_2$P(=S)N(isopropyl)P(phenyl)$_2$, but is not limited thereto.

The heteroatom ligand forming the transition metal catalyst according to the present invention may be prepared using various methods known to a person skilled in the art.

The transition metal catalyst according to the present invention may be mononuclear or binuclear, and specifically, may be represented by ML$^1$(L$^2$)$_p$(X)$_q$ or M$_2$X$^1{}_2$L$^1{}_2$(L$^2$)$_y$(X)$_z$ wherein M is a transition metal, L$^1$ is a heteroligand, L$^2$ is an organic ligand, X and X' are independently of each other a halogen, p is an integer of 0 or 1 or more, q is an integer of (oxidation number of M−p), y is an integer of 2 or more, and z is an integer of (2×oxidation number of M)−y−2.

Preferably, the transition metal catalyst according to an exemplary embodiment of the present invention may be represented by the following Chemical Formula 5 or 6, but is not limited thereto:

[Chemical Formula 5]

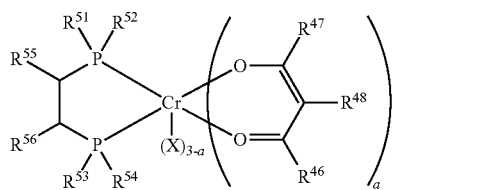

[Chemical Formula 6]

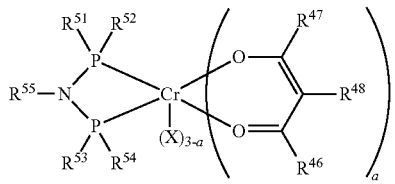

wherein $R^{46}$ to $R^{48}$ are independently of one another hydrogen, a halogen, (C6-C20)aryl, (C6-C20)ar(C1-C10)alkyl, (C1-C10)alkyl, halo(C1-C10)alkyl, (C6-C20)ar(C2-C10)alkenyl, (C2-C10)alkenyl, (C6-C20)ar(C2-C10)alkynyl, (C2-C10)alkynyl, (C1-C10)alkoxy, (C6-C20)aryloxy, (C1-C10)alkylcarbonyloxy, (C2-C10)alkenylcarbonyloxy, (C2-C10)alkynylcarbonyloxy, (C3-C7)cycloalkyl, (C1-C10)alkylsilyl, (C2-C10)alkenylsilyl, (C2-C10)alkynylsilyl, (C6-C20)arylsilyl, (C3-C20)heteroaryl, or 5- to 7-membered heterocycloalkyl;

the aryl, aralkyl, alkyl, aralkenyl, alkenyl, aralkynyl, alkynyl, alkoxy, aryloxy, cycloalkyl, heteroaryl, and heterocycloalkyl of $R^{46}$, $R^{47}$, and $R^{48}$ may be further substituted by one or more selected from the group consisting of (C1-C10)alkyl, (C2-C10)alkenyl, (C2-C10)alkynyl, (C1-C10)alkoxy, (C6-C20)aryl, (C6-C20)aryloxy, and halogens;

$R^{51}$ to $R^{54}$ are independently of one another (C6-C20)aryl, (C6-C20)ar(C1-C10)alkyl, (C6-C20)ar(C2-C10)alkenyl, (C6-C20)ar(C2-C10)alkynyl, (C1-C10)alkyl, (C2-C10)alkenyl, (C2-C10)alkynyl, (C1-C10)alkoxy, (C6-C20)aryloxy, (C1-C10)alkoxycarbonyl, (C1-C10)alkylcarbonyloxy, (C2-C10)alkenylcarbonyloxy, (C2-C10)alkynylcarbonyloxy, aminocarbonyl, (C1-C10)alkylcarbonylamino, (C2-C10)alkenylcarbonylamino, (C2-C10)alkynylcarbonylamino, (C3-C7)cycloalkyl, thio(C1-C10)alkyl, thio(C2-C10)alkenyl, thio(C2-C10)alkynyl, (C1-C10)alkylsilyl, (C2-C10)alkenylsilyl, (C2-C10)alkynylsilyl, (C6-C20)arylsilyl, (C3-C20)heteroaryl, 5- to 7-membered heterocycloalkyl, or —$NR^{21}R^{22}$, and $R^{21}$ and $R^{22}$ are independently of each other (C1-C10)alkyl, (C2-C10)alkenyl, (C2-C10)alkynyl, (C6-C20)aryl, di(C1-C10)alkylamino, di(C2-C10)alkenylamino, or di(C2-C10)alkynylamino;

$R^{55}$ and $R^{56}$ are independently of each other (C6-C20)aryl, (C6-C20)ar(C1-C10)alkyl, (C6-C20)ar(C2-C10)alkenyl, (C6-C20)ar(C2-C10)alkynyl, (C1-C10)alkyl, (C2-C10)alkenyl, (C2-C10)alkynyl, (C3-C7)cycloalkyl, (C3-C20)heteroaryl, 5- to 7-membered heterocycloalkyl, (C1-C10)alkoxy, (C6-C20)aryloxy, (C1-C10)alkoxycarbonyl, (C1-C10)alkylcarbonyloxy, (C2-C10)alkenylcarbonyloxy, (C2-C10)alkynylcarbonyloxy, aminocarbonyl, (C1-C10)alkylcarbonylamino, (C2-C10)alkenylcarbonylamino, (C2-C10)alkynylcarbonylamino, di(C1-C10)alkylamino, di(C2-C10)alkenylamino, di(C2-C10)alkynylamino, (C1-C10)alkylsilyl, (C2-C10)alkenylsilyl, (C2-C10)alkynylsilyl, or (C6-C20)arylsilyl, or $R^{45}$ and $R^{46}$ may be bonded via (C3-C10)alkylene or (C3-C10)alkenylene to form a ring;

the aryl, aralkyl, aralkenyl, aralkynyl, alkyl, alkenyl, alkoxy, aryloxy, alkoxycarbonyl, alkylcarbonyloxy, alkenylcarbonyloxy, alkynylcarbonyloxy, cycloalkyl, heteroaryl, and heterocycloalkyl of $R^{51}$ to $R^{54}$, and the aryl, aralkyl, aralkenyl, aralkynyl, alkyl, alkenyl, cycloalkyl, heteroaryl, heterocycloalkyl, alkoxy, aryloxy, alkoxycarbonyl, alkylcarbonyloxy, alkenylcarbonyloxy, alkynylcarbonyloxy, aminocarbonyl, alkylcarbonylamino, alkenylcarbonylamino, alkynylcarbonylamino, dialkylamino, dialkenylamino, dialkynylamino, alkylsilyl, alkenylsilyl, alkynylsilyl, or arylsilyl of $R^{55}$ and $R^{56}$ may be further substituted by one or more selected from the group consisting of (C1-C10)alkyl, (C2-C10)alkenyl, (C2-C10)alkynyl, (C1-C10)alkoxy, (C6-C20)aryloxy, di(C1-C10)alkylamino, di(C2-C10)alkenylamino, di(C2-C10)alkynylamino and halogens;

X is a halogen; and a is an integer of 0 or 1 to 3, b and c are independently of each other an integer of 1 or 2.

Preferably, the transition metal catalyst may be a compound of Chemical Formulae 5 and 6 wherein $R^{46}$ to $R^{48}$ are independently of one another hydrogen, (C1-C10)alkyl or halo(C1-C10)alkyl, $R^{51}$ to $R^{54}$ are independently of each other (C6-C20)aryl; $R^{55}$ and $R^{56}$ are independently of each other (C1-C10)alkyl, or a compound of Chemical Formulae 5 and 6 wherein $R^{51}$ to $R^{54}$ are independently of one another (C6-C20)aryl; $R^{55}$ and $R^{56}$ are independently of each other (C1-C10)alkyl, and a is 0.

The cocatalyst may be an organic aluminum compound, an organic aluminoxane, an organic boron compound, or a mixture thereof.

The organic aluminum compound may be a compound of $AlR3$ (wherein R is independently of each other (C1-C12) alkyl, (C2-C10)alkenyl, (C2-C10)alkynyl, (C1-C12)alkoxy, or a halogen) or $LiAlH_4$. However, the present invention is not limited thereto.

More specifically, the organic aluminum compound may be one or a mixture or two or more selected from the group consisting of trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride. However, the present invention is not limited thereto.

Though the present invention is not limited thereto, the organic aluminoxane may be an oligomer compound which may be prepared by adding water to trimethylaluminum. The thus-prepared aluminoxane oligomer compound may be linear, cyclic, cage, or a mixture thereof.

Specifically, the organic aluminoxane may be selected from the group consisting of alkylaluminoxane, for example, methylaluminoxane (MAO), ethylaluminoxane (EAO), tetraisobutylaluminoxane (TIBAO), and isobutylaluminoxane (IBAO), and also modified alkylaluminoxane, for example, modified methylaluminoxane (MAO). The modified methylaluminoxane (manufactured by Akzo Nobel N.V.) may include a hybrid alkyl group such as isobutyl or n-octyl groups in addition to a methyl group. However, the present invention is not limited thereto.

More specifically, the organic aluminoxane may be one or a mixture of two or more selected from the group consisting of methylaluminoxane (MAO), modified methylaluminoxane (MAO), ethylaluminoxane (EAO), tetraisobutylaluminoxane (TIBAO), and isobutylaluminoxane (IBAO). However, the present invention is not limited thereto.

Though the present invention is not limited thereto, the organic boron compound may be boroxine, $NaBH_4$, triethylborane, triphenylborane, a triphenylborane ammonia complex, tributylborate, triisopropylboate, tris(pentafluorophenyl)borane, trityl(tetrapentafluorophenyl)borate, dimethylphenylammonium(tetrapentafluorophenyl)borate, diethylphenylammonium(tetrapentafluorophenyl)borate, methyldiphenylammonium(tetrapentafluorophenyl)borate, or ethyldiphenylammonium(tetrapentafluorophenyl)borate, and the organic boron compound thereof may be mixed with the organic aluminum compound or the organic aluminoxane.

In addition, the linear α-olefin preparation process may further include a step of introducing a catalyst deactivator to a reaction product of the oligomerization reaction after the step of performing the oligomerization reaction.

The catalyst deactivator is introduced for controlling an unnecessary side reaction at the end of the reactor during preparation of the linear α-olefin and terminating the reaction, and in an embodiment of the present invention, the catalyst deactivator may include an oxygen-containing inorganic material which is in a gaseous state at 25° C. and 1 atm; or an organic compound which includes one or more of functional groups containing at least one selected from the group consisting of oxygen, phosphorus, nitrogen, and sulfur, and has a number average molecular weight of 400 or more.

In the case in which the catalyst deactivator as described above is used in the linear α-olefin preparation process, when paraffin is purified after preparation of paraffin of the present invention, separation efficiency may be improved to save process energy.

Specifically, when a catalyst deactivator including an oxygen-containing inorganic material which is in a gaseous state at 25° C. and 1 atm, is used, a difference in a boiling point when separation and purification with paraffin is large, and thus, the catalyst deactivator may be separated and removed by a separation process such as simple distillation.

Even the catalyst deactivator including an organic compound which includes one or more of the functional groups containing at least one selected from the group consisting of oxygen, phosphorus, nitrogen, and sulfur and has a number average molecular weight of 400 or more, may be separated and removed only with introduction of low energy during distillation, by a compound having a higher boiling point than the prepared paraffins.

Thus, the process efficiency of the paraffin preparation process of an embodiment of the present invention may be further increased, which may be preferred. However, the present invention is not necessarily limited thereto, and even in the case in which the boiling point of the catalyst deactivator is positioned between the boiling points of paraffin to be prepared, separation may be performed by adding a separate separation process or under different conditions.

The oxygen-containing inorganic material may be, as a non-limiting example, $O_2$, $CO_2$, CO, $H_2O$, $NO_x$, $SO_x$, or a mixture thereof. Specifically, the oxygen-containing inorganic material may be $O_2$, $CO_2$, CO, or a mixture thereof, and more specifically, $CO_2$ and $O_2$. More specifically, since $CO_2$ may be available at low cost as a material occurring as a by-product or exhaust gas in many industry fields, it may be preferred in terms of improving process economic feasibility.

Here, $NO_x$ may be, for example, NO, $NO_2$, $N_2O$, $N_2O_3$, $N_2O_4$, $N_2O_5$, or a mixture thereof, but the present invention is not limited thereto.

$SO_x$ may be $SO_2$, $SO_3$, or a mixture thereof, but the present invention is not limited thereto.

The organic compound may have a number average molecular weight of specifically 600 or more, 700 or more, or 1000 or more.

The upper limit of the number average molecular weight of the organic compound may be 10,000 or less, 5,000 or less, or 2,000 or less, but is not limited thereto.

The organic compound may include one or more of the functional groups containing any one selected from the group consisting of oxygen, phosphorus, nitrogen, and sulfur, and as a specific embodiment, the organic compound may include one functional group containing one of four elements singularly or plurally, or two or more functional groups of the functional groups containing one of four elements singularly or plurally. This is illustrative, and the present invention is not limited thereto.

The specific kind of organic compound may be a phosphine-based compound of C31 or higher, an amine-based compound of C31 or higher, a thiol-based compound of C31 or higher, an alcohol-based compound of C31 or higher, an ether-based compound of C31 or higher, an ester-based compound of C31 or higher, a carboxylic acid of C31 or higher, or a ketone-based compound of C31 or higher.

More specifically, the organic compound may be a phosphine-based compound of C31 or higher, an amine-based compound of C31 or higher, a thiol-based compound of C31 or higher, or an alcohol-based compound of C31 or higher.

Still more specifically, the organic compound may be polypropylene glycol (PPG) represented by the following Chemical Formula 1:

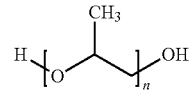

[Chemical Formula 1]

wherein n is 11 or more and 170 or less.

In Chemical Formula 1, n is more specifically 12 or more and 150 or less, 17 or more and 130 or less, 17 or more and 110 or less, 17 or more and 35 or less, or 16 or more and 35 or less.

The catalyst deactivator of the present invention is not necessarily limited, but the polypropylene glycol compound has a better catalyst deactivation effect than the polyethylene glycol compound, among the alcohol-based compounds, and may be easily separated from the linear α-olefin in the oligomerization reaction product of olefin, and thus, is preferred.

The olefin monomer is not particularly limited, and may be, for example, ethylene, propylene, or butene.

Hereinafter, the preferred Examples and Comparative Examples of the present invention will be described. However, the following Examples are only a preferred example, and the present invention is not limited thereto.

PREPARATION EXAMPLE

Bis-[(S,S)-(phenyl)$_2$PCH(methyl)CH(methyl)P(phenyl)$_2$ chromium dichloride (μ-chloride)] (5.3 μmol-Cr) as a catalyst for oligomerization of ethylene was prepared by the following method.

2.1 mg (5.3 umol) of tris(tetrahydrofuran) chromium trichloride (CrCl$_3$(THF)$_3$) was dissolved in 1 mL of methane dichloride, and to this solution, a solution in which 2.4 mg (5.6 umol) of a (S,S)-(phenyl)$_2$PCH(methyl)CH(methyl)P (phenyl)$_2$ ligand compound is dissolved in 1 mL of methane dichloride was slowly added and reacted for 60 minutes. Thereafter, the reactants were further stirred for 5 minutes, and 1.3 mg (5.6 umol) of sodium hexafluoroacetylacetonate was slowly added. Next, the reactants were further stirred for 3 hours, and filtered using a 0.2 um syringe filter. A volatile matter was removed from the filtrate to obtain a dry dark green solid, which was prepared as an oligomerization catalyst of the examples described later.

This catalyst has excellent activity and selectivity of the oligomerization reaction of ethylene, and may be more clearly grasped, referring to Korean Patent Application No. 10-2016-0065709.

Example 1

A 5.6 L stainless steel pressure reactor was washed with nitrogen under vacuum, methylcyclohexane (MCH) was introduced as a solvent at a rate of 2.0 kg/hr, the pressure was applied to 60 kg/cm²g, and the temperature was raised to 60° C. Methyl aluminoxane (MAO, Albemarle Corporation, 1.2 mmol/L MCH) and trimethylaluminum (TMA, Sigma-Aldrich Corporation, 1.2 mmol/L MCH) as a cocatalyst were introduced, 2 μmol/L MCH of bis-[(S,S)-(phenyl)$_2$PCH(methyl)CH(methyl)P(phenyl)$_2$ chromium dichloride (p-chloride)] prepared in the Preparation Example was introduced, 600 g/h of ethylene was continuously supplied, the temperature was controlled in an external jacket cooling manner, and hydrogen was introduced at a flow rate of 1 g/kg of ethylene, thereby performing the ethylene oligomerization reaction. At a latter part of the reactor, 2-ethylhexanol (Sigma-Aldrich Corporation) as a catalyst deactivator was introduced at 10 equivalents to the moles of aluminum in the introduced cocatalyst, thereby inhibiting catalytic activity so that an additional side reaction is not caused.

Thereafter, from the thus-obtained product, a component of C10 or higher was first separated at 145° C. or higher under normal pressure by distillation, and a polymer component was removed at 300° C. Detailed analysis of the C10 and C12 components in the separated material was performed by GC-FID and 2D-GC. Olefins in the component were classified into a branched α-olefin, a branched internal olefin, a linear α-olefin, and a linear internal olefin, and the results of quantitatively analyzing other components are as shown in Table 1. It is recognized that C10 accounts for 36 wt %, C12 accounts for 45 wt % in the entire components, which account for a total of 80 wt % or more, and the obtained product may include about 80 to 90 mol % of the branched olefin, 4 to 12 mol % of the linear olefin, and 2 to 5 mol % of the naphthene and paraffin components.

TABLE 1

| | mol % | |
|---|---|---|
| Classification | C10 | C12 |
| Branched Alpha Olefin | 70.68 | 71.28 |
| Branched Internal Olefin | 11.86 | 19.17 |
| Linear Alpha Olefin | 6.20 | 4.60 |
| Linear Internal Olefin | 3.90 | 0.00 |
| Naphthene | 3.77 | 1.47 |
| Normal Paraffin | 1.10 | 1.07 |
| Unknown | 2.49 | 2.40 |
| Total | 100.00 | 100.00 |

A 15 mL of stainless steel reactor was fully filled with hydrogenation catalyst (Ni/Alumina support catalyst, 15 to 30 wt % of Ni), hydrogen was filled thereinto at 120° C. at 35 kg/cm²g, and the product obtained from above was injected at 0.4 cc/min in the form of a trickle bed reaction, thereby performing hydrogenation. After the hydrogenation, GC analysis was performed in the same manner as in the above, and as a result, it was confirmed that the olefin component was not detected and was all converted into paraffin.

After performing hydrogenation, 2-ethylhexanol, which has a boiling point overlapping the boiling point of C10 materials, was extracted using acetonitrile and removed. The thus-obtained C10-C18 components were divided into 11 fractions in the distillation tower having 60 columns, and color (ASTM D156), density (ASTM D4052), aniline point (ASTM D611), viscosity (ASTM D445), distillation (ASTM D86), bromine index (ASTM D1492), and aromatic content (GC-FID) were measured, and as a result, it was confirmed that the measurement values satisfy the commercially available iso-paraffin product specification, as shown in Table 2.

TABLE 2

| Fraction | #1 | #2 | #3 | #4 | #5 | #6 | #7 | #8 | #9 | #10 | #11 |
|---|---|---|---|---|---|---|---|---|---|---|---|
| Color, Saybolt | | | | | | 30 | | | | | |
| Density 15.56/15.56° C. | 0.737 | 0.7533 | 0.7553 | 0.755 | 0.755 | 0.755 | 0.755 | 0.756 | 0.763 | 0.771 | 0.769 |
| Aniline Point, ° C. | | 81 | 83 | 83 | 83 | 33 | 83 | 83 | 83 | 86 | 88 |
| Viscosity, 40° C. cSt | 0.85 | 1.16 | 1.23 | 1.30 | 1.31 | 1.31 | 1.32 | 1.34 | 1.45 | 1.79 | 1.90 |
| Distillation, IBP-FBP, ° C. | | 158-209 | | 195-205 | 198-205 | 193-207 | 200-207 | 199-208 | 200-208 | 204-219 | 224-237 | 228-240 |
| Bromine Index, mg/100 g | | | | | | <10 | | | | | |
| Aromatic Content, wt % | | | | | | <0.01 | | | | | |

DETAILED DESCRIPTION OF MAIN ELEMENTS

10: Linear α-olefin preparation process
20: Hydrogenation process
30: Iso-paraffin purification process
40: Linear α-olefin preparation reactor
50: Injection line
60: Outflow line 70: Catalyst deactivator injection line
80: Distiller
90: Recirculation line

The invention claimed is:

1. A preparation method of a paraffin, the method comprising:
performing a linear α-olefin preparation process to prepare a linear α-olefin and by-products comprising 30 to 95 mol % of a branched olefin, 0 to 50 mol % of a linear internal olefin, and a balance of other by-products comprising iso-paraffin, n-paraffin, naphthene, or a combination thereof, based on a total of 100 mol % of the by-products;
providing a feed comprising the by-products; and
hydrogenating the feed,
wherein the branched olefin comprise a C10 branched olefin and a C12 branched olefin, and
wherein the linear a-olefin preparation process comprises a step of oligomerizing an olefin monomer in the presence of a transition metal catalyst comprising an acetylacetonate-based ligand represented by the following Chemical Formula 2, and a heteroatom ligand having a P—C—C—P skeleton structure represented by the following Chemical Formula 3 or a P—N—P skeleton structure represented by the following Chemical Formula 4:

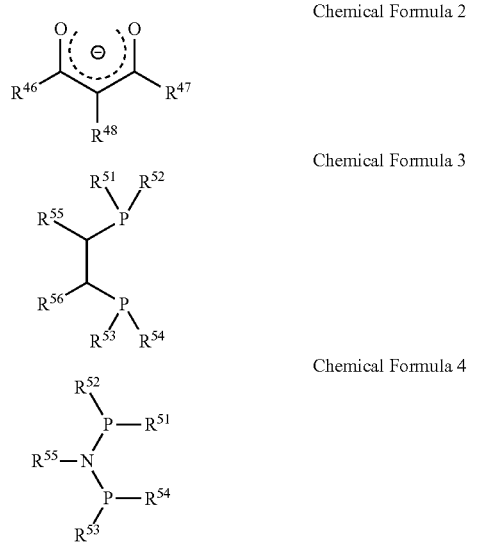

Chemical Formula 2

Chemical Formula 3

Chemical Formula 4 wherein
$R^{46}$ to $R^{48}$ are independently of one another hydrogen, a halogen, (C6-C20)aryl, (C6-C20)ar(C1-C10)alkyl, (C1-C10)alkyl, halo(C1-C10)alkyl, (C6-C20)ar(C2-C10)alkenyl, (C2-C10)alkenyl, (C6-C20)ar(C2-C10)alkynyl, (C2-C10)alkynyl, (C1-C10)alkoxy, (C6-C20)aryloxy, (C1-C10)alkylcarbonyloxy, (C2-C10)alkenylcarbonyloxy, (C2-C10)alkynylcarbonyloxy, (C3-C7)cycloalkyl, (C1-C10)alkylsilyl, (C2-C10)alkenylsilyl, fluorine-substituted (C2-C10)alkynylsilyl, (C6-C20)arylsilyl, (C3-C20)heteroaryl, or 5- to 7-membered heterocycloalkyl;
the aryl, aralkyl, alkyl, aralkenyl, alkenyl, aralkynyl, alkynyl, alkoxy, aryloxy, cycloalkyl, heteroaryl, and heterocycloalkyl of $R^{46}$ to $R^{48}$ may be further substituted by one or more selected from the group consisting of (C1-C10)alkyl, (C2-C10)alkenyl, (C2-C10)alkynyl, (C1-C10)alkoxy, (C6-C20)aryl, (C6-C20)aryloxy, and halogens;
$R^{51}$ to $R^{54}$ are independently of one another (C6-C20)aryl, (C6-C20)ar(C1-C10)alkyl, (C6-C20)ar(C2-C10)alkenyl, (C6-C20)ar(C2-C10)alkynyl, (C1-C10)alkyl, (C2-C10)alkenyl, (C2-C10)alkynyl, (C1-C10)alkoxy, (C6-C20)aryloxy, (C1-C10)alkoxycarbonyl, (C1-C10) alkylcarbonyloxy, (C2-C10)alkenylcarbonyloxy, (C2-C10)alkynylcarbonyloxy, aminocarbonyl, (C1-C10)alkylcarbonylamino, (C2-C10)alkenylcarbonylamino, (C2-C10)alkynylcarbonylamino, (C3-C7)cycloalkyl, thio(C1-C10)alkyl, thio(C2-C10)alkenyl, thio(C2-C10)alkynyl, (C1-C10)alkylsilyl, (C2-C10)alkenylsilyl, (C2-C10)alkynylsilyl, (C6-C20)arylsilyl, 5- to 7-membered heterocycloalkyl, or —$NR^{61}R^{62}$, and $R^{61}$ and $R^{62}$ are independently of each other (C1-C10)alkyl, (C2-C10)alkenyl, (C2-C10)alkynyl, (C6-C20)aryl, di(C1-C10)alkylamino, di(C2-C10)alkenylamino, or di(C2-C10)alkynylamino;
the aryl, aralkyl, aralkenyl, aralkynyl, alkyl, alkenyl, alkoxy, aryloxy, alkoxycarbonyl, alkylcarbonyloxy, alkenylcarbonyloxy, alkynylcarbonyloxy, cycloalkyl, heteroaryl, and heterocycloalkyl of $R^{51}$ to $R^{54}$ may be further substituted by one or more selected from the group consisting of (C1-C10)alkyl, (C2-C10)alkenyl, (C2-C10)alkynyl, (C1-C10)alkoxy, (C6-C20)aryloxy, di(C1-C10)alkylamino, di(C2-C10)alkenylamino and di(C2-C10)alkynylamino; and
$R^{55}$ and $R^{56}$ are independently of each other hydrocarbyl or substituted hydrocarbyl, or $R^{55}$ and $R^{56}$ may be bonded to each other via hydrocarbylene, substituted hydrocarbylene, heterohydrocarbylene, or substituted heterohydrocarbylene to form a ring.

2. The preparation method of paraffin of claim 1, wherein the feed is directly hydrogenated.

3. The preparation method of paraffin of claim 1, wherein the by-products include 60 to 95 mol % of the branched olefin and 1 to 20 mol % of the linear internal olefin.

4. The preparation method of paraffin of claim 1, wherein the hydrogenating is performed in a trickle bed reactor.

5. The preparation method of paraffin of claim 4, wherein the feed flows into the trickle bed reactor in a liquid phase, a space velocity (SV) at which the feed flows in is 0.1 to 4 $h^{-1}$, and the SV is calculated by dividing an inflow rate ($m^3$/h) of the liquid feed by a reaction volume ($m^3$) in the trickle bed reactor.

6. The preparation method of paraffin of claim 1, wherein the hydrogenating is performed at a temperature of 100 to 200° C. under a pressure of 10 to 100 kg/cm²g under a metal catalyst selected from the group consisting of nickel (Ni), platinum (Pt), palladium (Pd), rhodium (Rh), ruthenium (Ru), and an alloy containing two or more thereof.

7. The preparation method of paraffin of claim 1, further comprising: after the hydrogenating, separating a prepared paraffin from a reaction product of the hydrogenation reaction.

8. The preparation method of paraffin of claim 1, further comprising: after the hydrogenating, separating iso-paraffin from the prepared paraffin.

9. The preparation method of paraffin of claim 1, further comprising: after the oligomerizing, introducing a catalyst deactivator to a reaction product of the oligomerization reaction.

10. The preparation method of paraffin of claim 9, wherein the catalyst deactivator comprises an oxygen-containing inorganic material which is in a gaseous state at 25°

C. and 1 atm, or an organic compound which includes one or more of functional groups containing at least one selected from the group consisting of $H_2O$, 2-ethylhexanol, oxygen, phosphorus, nitrogen, and sulfur, and has a number average molecular weight of 400 or more.

11. The preparation method of paraffin of claim 10, wherein the catalyst deactivator comprises an oxygen-containing inorganic material which is in a gaseous state at 25° C. and 1 atm; or an organic compound which includes one or more of functional groups containing at least one selected from the group consisting of oxygen, phosphorus, nitrogen, and sulfur, and has a number average molecular weight of 400 or more.

12. The preparation method of paraffin of claim 11, wherein the oxygen-containing inorganic material is $O_2$, $CO2$, $CO$, $NO$, $NO_2$, $N_2O$, $N_2O_3$, $N_2O_4$, $N_2O_5$, $SO_2$, $SO_3$, or a mixture thereof.

* * * * *